United States Patent
Kubo et al.

(10) Patent No.: US 7,799,949 B2
(45) Date of Patent: Sep. 21, 2010

(54) TETRAPHENYLMETHANE SKELETON-CONTAINING COMPOUND

(75) Inventors: Youhei Kubo, Shizuoka (JP); Koki Nakamura, Kanagawa (JP); Katsuyuki Watanabe, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/397,684

(22) Filed: Mar. 4, 2009

(65) Prior Publication Data

US 2009/0227812 A1    Sep. 10, 2009

(30) Foreign Application Priority Data

Mar. 7, 2008   (JP)   .............................. 2008-058312

(51) Int. Cl.
C09B 11/02   (2006.01)
C07C 211/00   (2006.01)
C07C 205/00   (2006.01)

(52) U.S. Cl. ......................... 564/322; 568/706; 564/305
(58) Field of Classification Search ....................... None
See application file for complete search history.

(56) References Cited

U.S. PATENT DOCUMENTS

2003/0055278 A1\* 3/2003 Bazan et al. ................ 558/411

FOREIGN PATENT DOCUMENTS

JP   2003-206278 A   7/2003
JP   2004-059557 A   2/2004
JP   2005-60626 A   3/2005

OTHER PUBLICATIONS

Weissberger, A. Journal of the Chemical Society (1934) 148-151 (Derwent Abstract).\*

\* cited by examiner

*Primary Examiner*—Daniel M Sullivan
*Assistant Examiner*—Clinton Brooks
(74) *Attorney, Agent, or Firm*—Sughrue Mion, PLLC

(57) ABSTRACT

A compound represented by the formula below is provided.

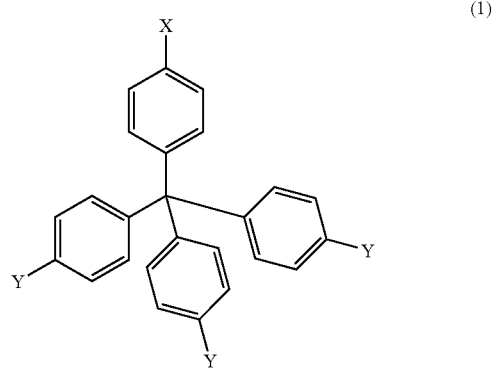

(1)

(In the formula, X and Y denote a hydroxy group, an amino group, or a halogen atom, and X and Y are groups that are different from each other.)

2 Claims, No Drawings

TETRAPHENYLMETHANE SKELETON-CONTAINING COMPOUND

TECHNICAL FIELD

The present invention relates to a novel tetraphenylmethane skeleton-containing compound.

BACKGROUND ART

In recent years, tetraphenylmethane skeleton-containing compounds have been attracting attention in various fields and, for example, the cases below are known.

JP-A-2005-60626 (JP-A denotes a Japanese unexamined patent application publication) discloses a macromolecular compound, obtained by a three-dimensional crosslinking reaction of a compound represented by Formula (1) below, which can be used in an interlayer insulating film or a liquid crystal alignment film.

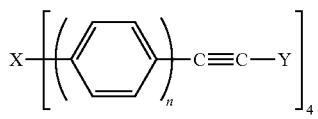

(1)

(In Formula (1), X is a tetravalent organic group having 1 to 10 carbon atoms or a silicon atom; each Y is independently a hydrogen atom or a monovalent organic group having 1 to 10 carbon atoms; and each n is independently 0 or a positive integer.)

Furthermore, JP-A-2003-206278 discloses a tetraphenylmethane derivative represented by General Formula (1) below, which can be used in a light emitting device.

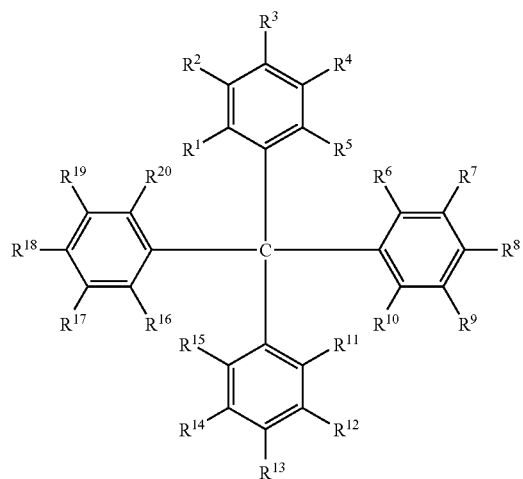

(1)

(Here, $R^1$ to $R^{20}$ are selected from hydrogen, an alkyl group, a cycloalkyl group, an aralkyl group, an alkenyl group, a cycloalkenyl group, an alkynyl group, a hydroxy group, a mercapto group, an alkoxy group, an alkylthio group, an aryl ether group, an aryl thioether group, an aryl group, a heterocyclic group, a halogen, a haloalkane, a haloalkene, a haloalkyne, a cyano group, an aldehyde group, a carbonyl group, a carboxyl group, an ester group, a carbamoyl group, an amino group, a nitro group, a silyl group, a siloxanyl group, and a ring structure formed between adjacent substituents, provided that at least one of $R^1$ to $R^5$ and at least one of $R^6$ to $R^{10}$ are a pyridine ring skeleton-containing substituent.)

Furthermore, JP-A-2004-59557 discloses a compound represented by General Formula (1) below, which may be used in an electrophotographic photoreceptor, an organic electroluminescent device, and various types of organic semiconductor devices.

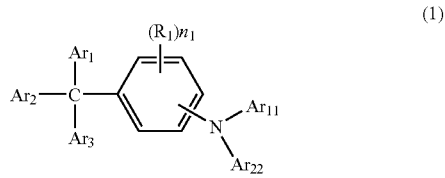

(1)

(Here, in the formula above, $R_1$ denotes an unsubstituted or substituted alkyl group or an unsubstituted or substituted alkoxy group, and $n_1$ denotes an integer of 0, 1, 2, 3, or 4. When $n_1$ is an integer of 2 or greater, the $R_1$s are a plurality of identical substituents or a plurality of different substituents. $Ar_1$, $Ar_2$, $Ar_3$, $Ar_{11}$, and $Ar_{22}$ are mutually identical or different groups and denote an unsubstituted or substituted aromatic hydrocarbon group.)

DISCLOSURE OF INVENTION

Problems to be Solved by the Invention

It is an object of the present invention to provide a novel tetraphenylmethane skeleton-containing compound.

Means for Solving the Problems

The above-mentioned object has been attained by <1> below. It is described together with <2> to <6>, which are preferred embodiments.

<1> A compound represented by Formula (1) below

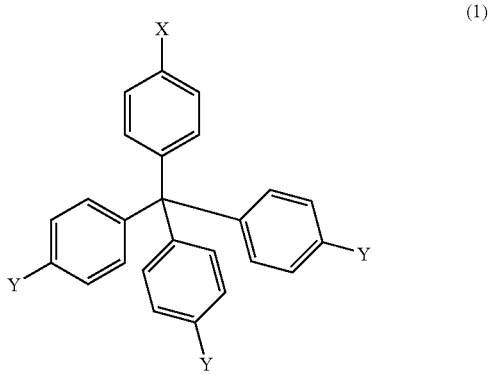

(1)

(in Formula (1), X and Y denote a hydroxy group, an amino group, or a halogen atom, and X and Y are groups that are different from each other), <2> the compound according to <1> above, wherein it is a compound represented by Formula (1-1) to Formula (1-4) below, (1-1)

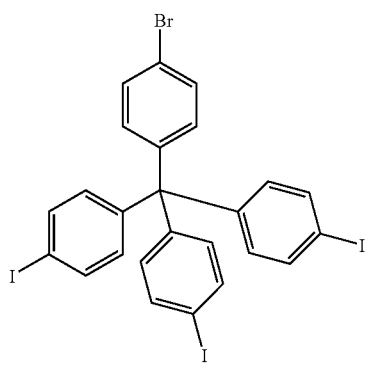

(1-2)

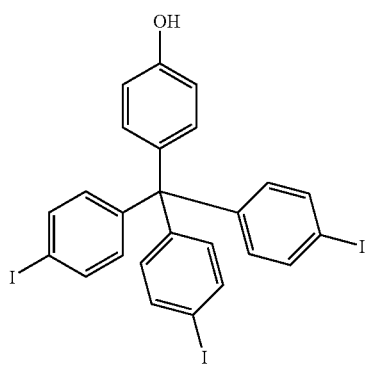

(1-3)

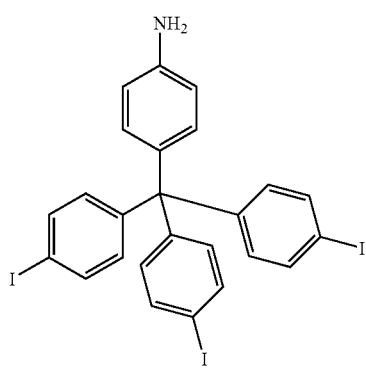

(1-4)

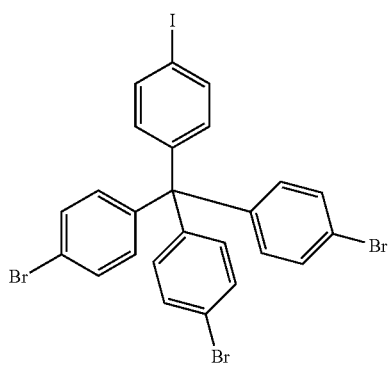

<3> the compound according to <1> or <2> above, wherein it is a compound represented by Formula (1-1) below, (1-1)

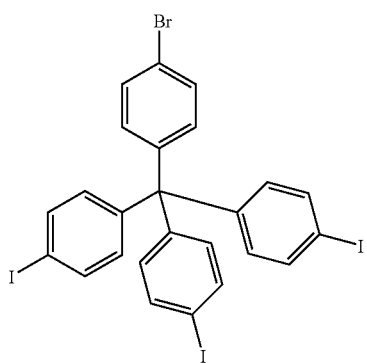

<4> the compound according to <1> or <2> above, wherein it is a compound represented by Formula (1-2) below, (1-2)

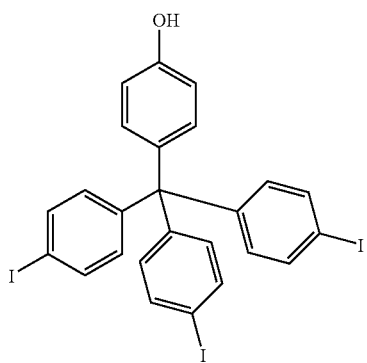

<5> the compound according to <1> or <2> above, wherein it is a compound represented by Formula (1-3) below, (1-3)

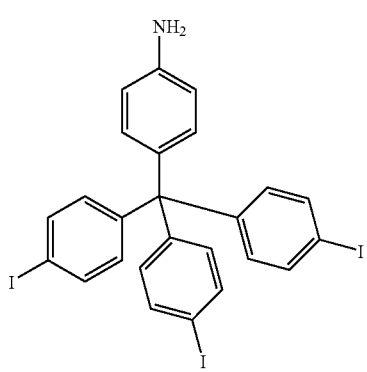

and

<6> the compound according to <1> or <2> above, wherein it is a compound represented by Formula (1-4) below.

(1-4)

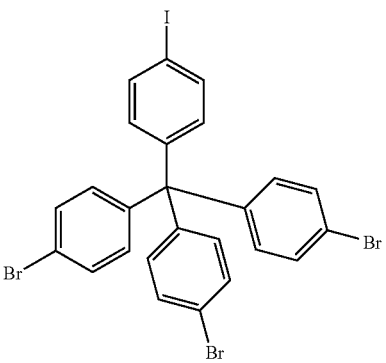

BEST MODE FOR CARRYING OUT THE INVENTION

The present invention is explained in detail below.

The compound of the present invention is a compound represented by Formula (1) below.

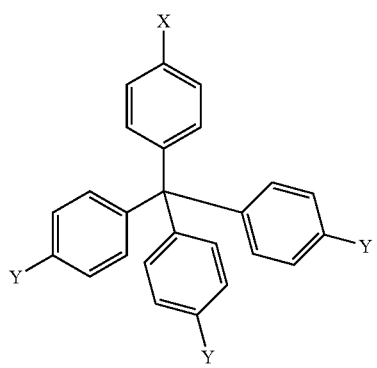

(In Formula (1), X and Y denote a hydroxy group, an amino group, or a halogen atom, and X and Y are groups that are different from each other.)

With regard to the compound of the present invention, since, among the four benzene rings of the tetraphenylmethane skeleton, one benzene ring has substituent X, which is selected from the group consisting of a hydroxy group, an amino group, and a halogen atom, and the other three benzene rings have substituent Y, which is different from substituent X, substituent X and substituent Y may each further be readily derivatized to a different group, and it is thus possible to readily synthesize a compound having at least two types of groups in the tetraphenylmethane skeleton and having high heat resistance. Furthermore, by introducing into substituent X and/or substituent Y, for example, an ethylenically unsaturated double bond- or triple bond-containing group, it is possible to readily prepare a novel monomer having high heat resistance and a novel resin formed by polymerizing same.

Moreover, since the compound of the present invention has substituents introduced into the tetraphenylmethane skeleton at a ratio of 3:1, by selecting the substituents it is possible to readily synthesize a molecule having a plurality of tetraphenylmethane skeletons in the molecule.

Furthermore, using the compound of the present invention as a starting material, it is possible to readily link an acetylene compound, an olefin compound, an aromatic compound, etc. by a Sonogashira reaction, a Suzuki coupling reaction, a Heck reaction, or a Stille reaction.

As hereinbefore described, the compound of the present invention may suitably be used as an intermediate when synthesizing various types of tetraphenylmethane skeleton-containing compounds.

Furthermore, the compound of the present invention may particularly suitably be used as an intermediate for a crosslinking agent or an intermediate for a high heat resistance material.

A high heat resistance material formed using the compound of the present invention as a starting material may be used in various applications where heat resistance is required. Specific examples thereof include electronic materials, fibers, printed circuits, pressure-sensitive adhesive tape, magnetic recording media, electric wire, heat-resistant insulating paper, paint, casting materials, printed wiring boards, and molding materials.

X in Formula (1) above denotes a hydroxy group, an amino group, or a halogen atom (a fluorine atom, a chlorine atom, a bromine atom, or an iodine atom); a hydroxy group, an amino group, an iodine atom, or a bromine atom is preferable, and a hydroxy group or an amino group is more preferable.

Y in Formula (1) above denotes a hydroxy group, an amino group, or a halogen atom (a fluorine atom, a chlorine atom, a bromine atom, or an iodine atom); a hydroxy group, an amino group, an iodine atom, or a bromine atom is preferable, and an iodine atom or a bromine atom is more preferable.

X and Y in Formula (1) above are groups that are different from each other.

A combination of X and Y in Formula (1) above may be selected appropriately as desired, but it is preferable that X is a hydroxy group, an amino group, or a halogen atom and Y is a halogen atom, it is more preferable that X is a hydroxy group, an amino group, an iodine atom, or a bromine atom and Y is an iodine atom or a bromine atom, and it is yet more preferable that X is a hydroxy group or an amino group and Y is an iodine atom or a bromine atom.

Specific examples of the compound represented by Formula (1) above include the compounds given below.

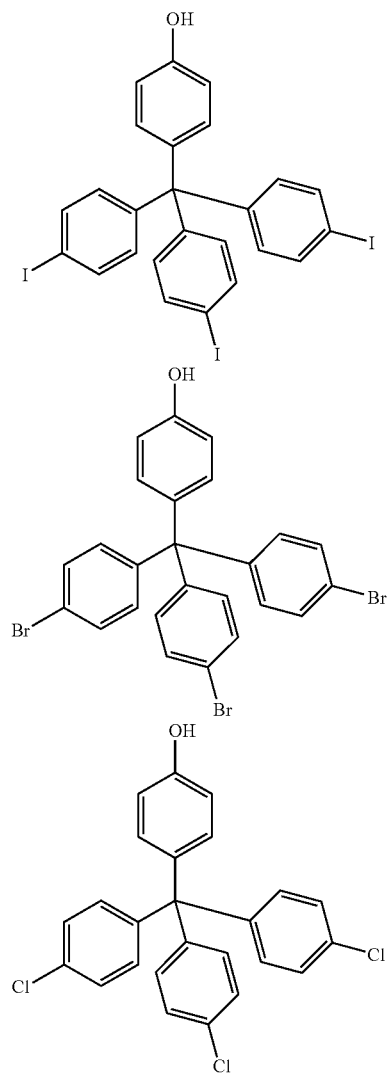

-continued
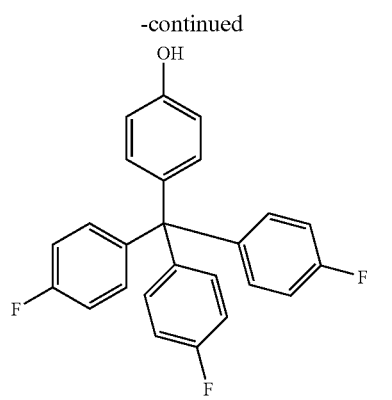
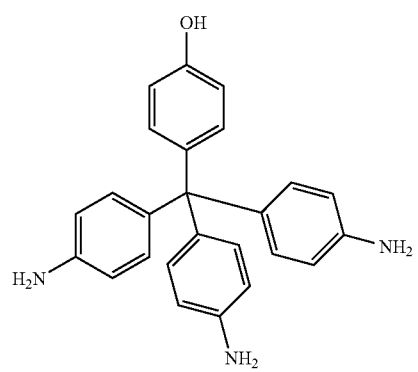
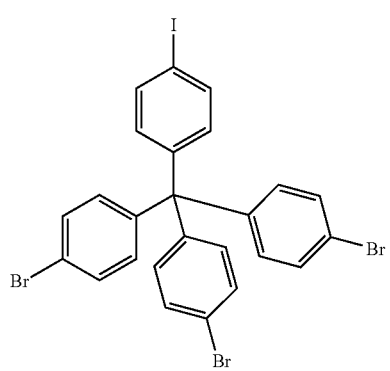
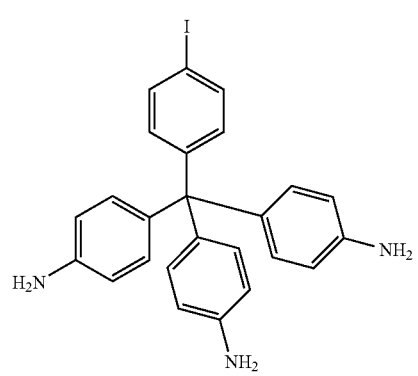
-continued
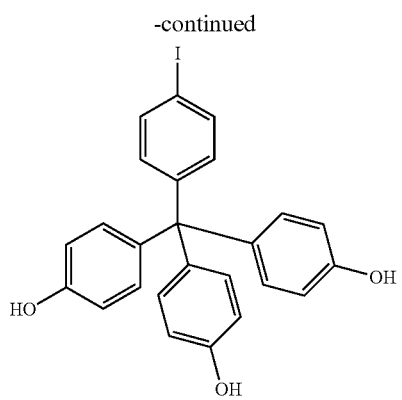
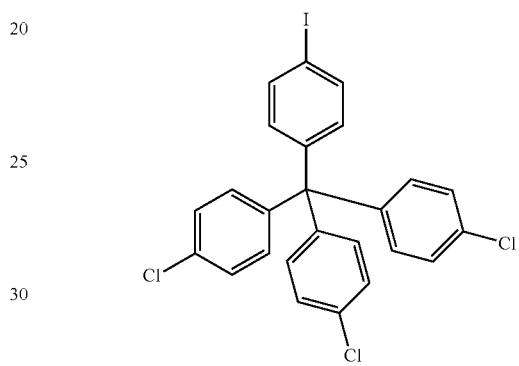
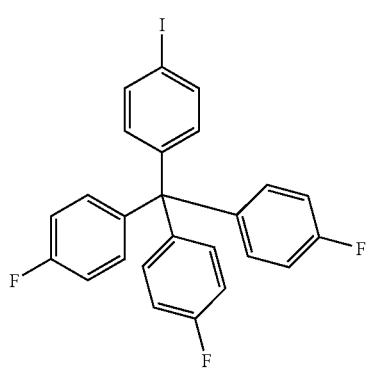
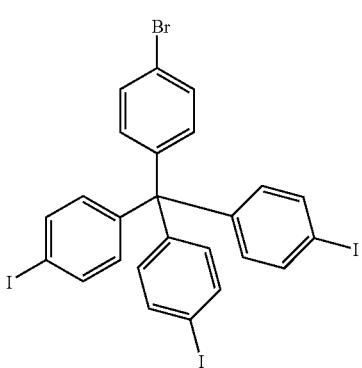

-continued
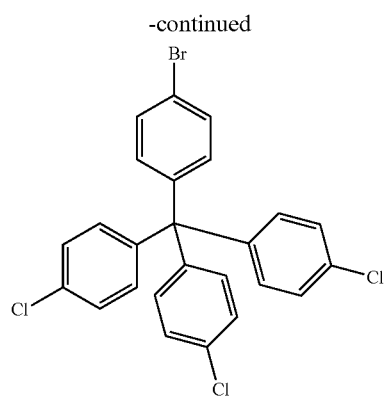
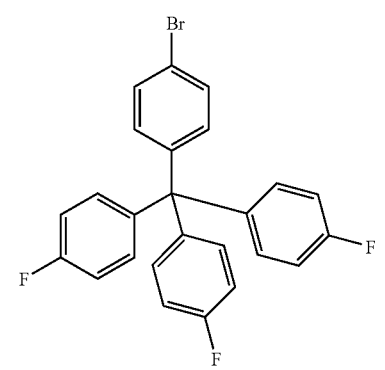
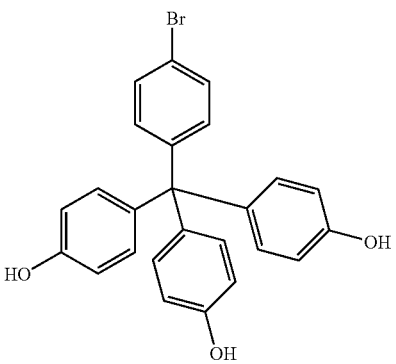
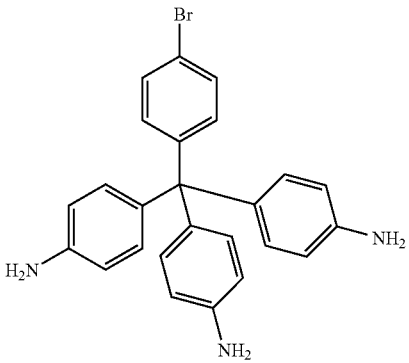
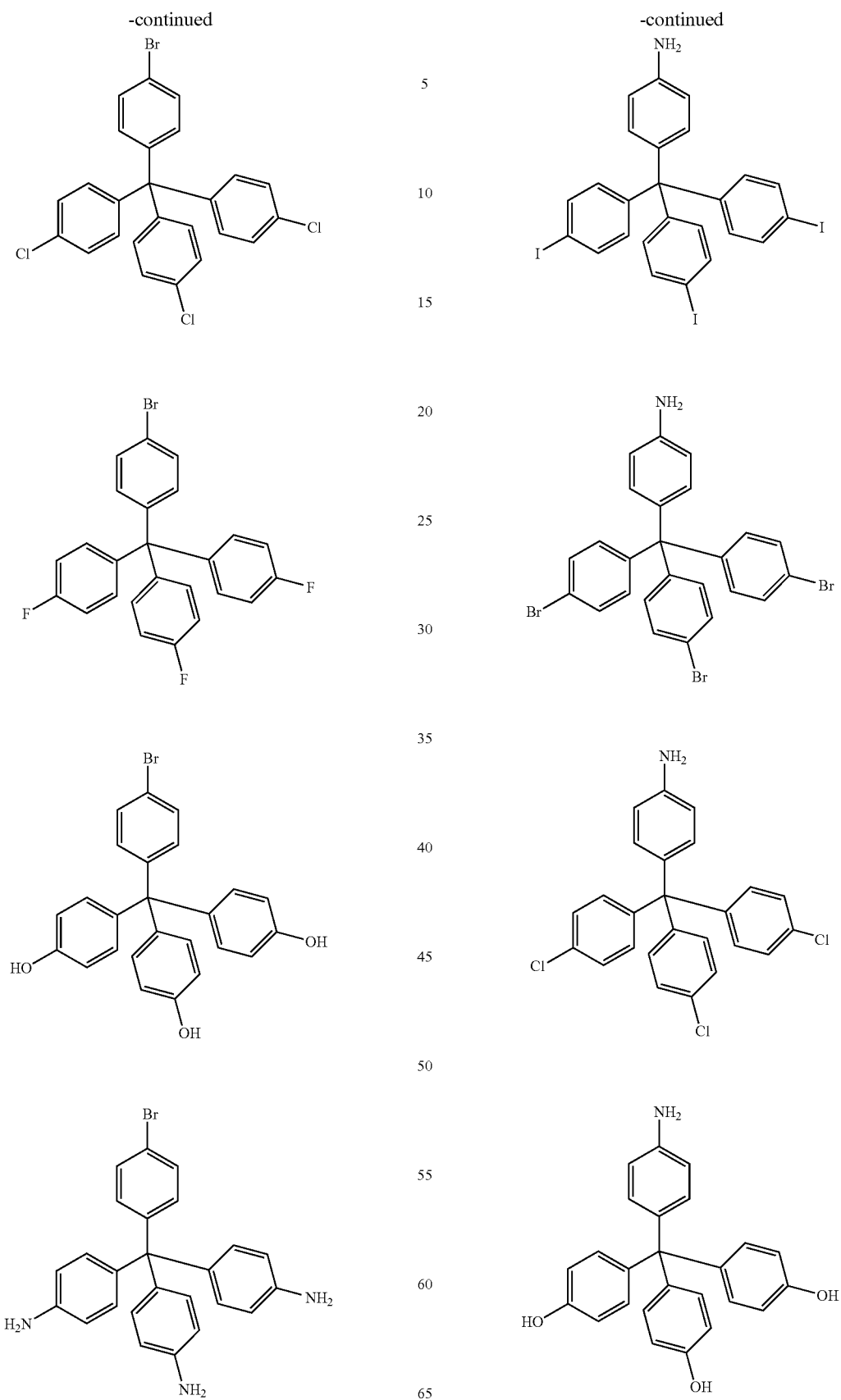

-continued
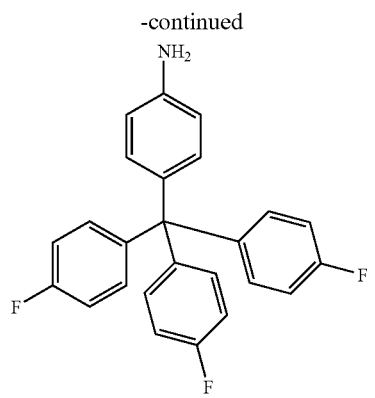
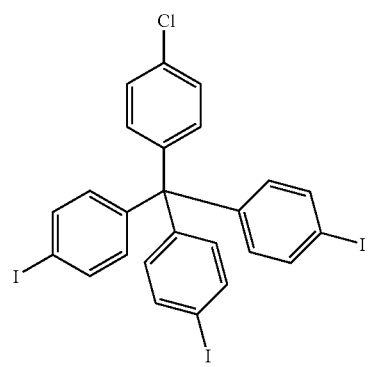
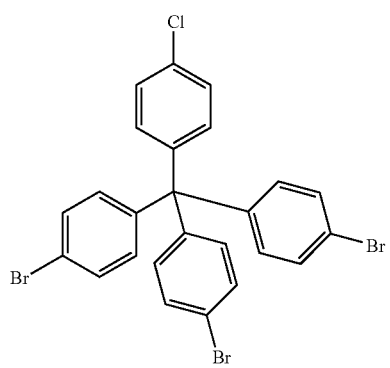
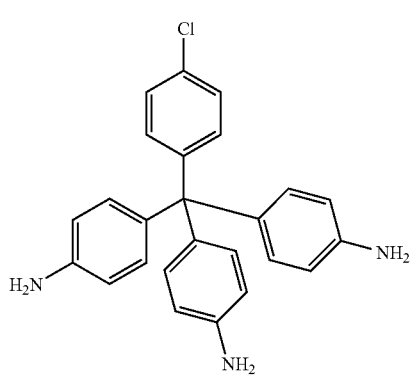
-continued
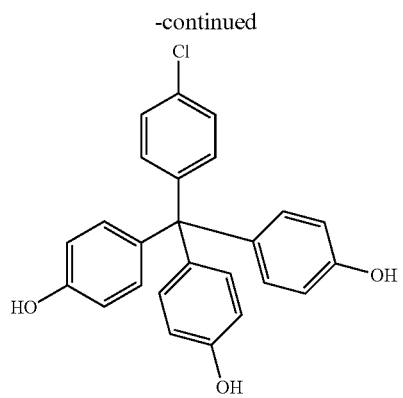
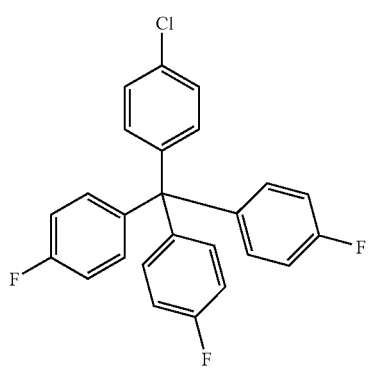
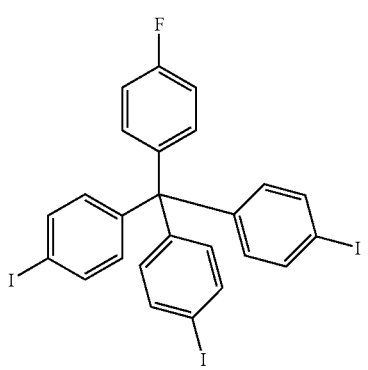
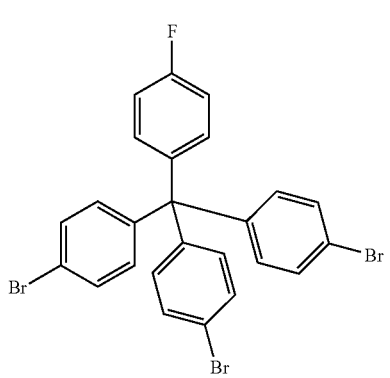

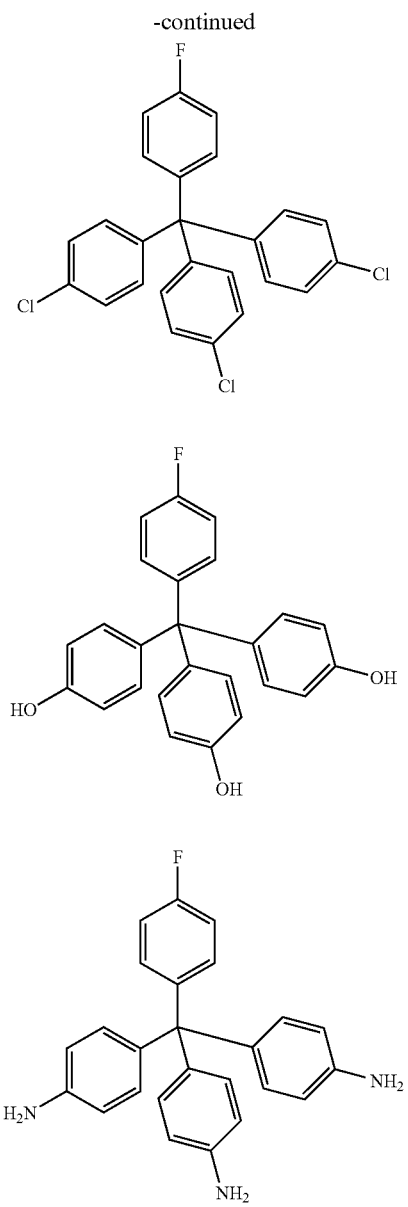

Among them, compounds represented by Formula (1-1) to Formula (1-4) below can be cited as preferred examples.

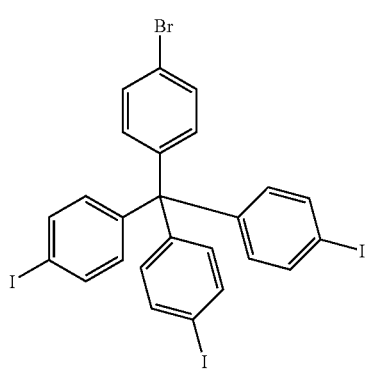

(1-1)

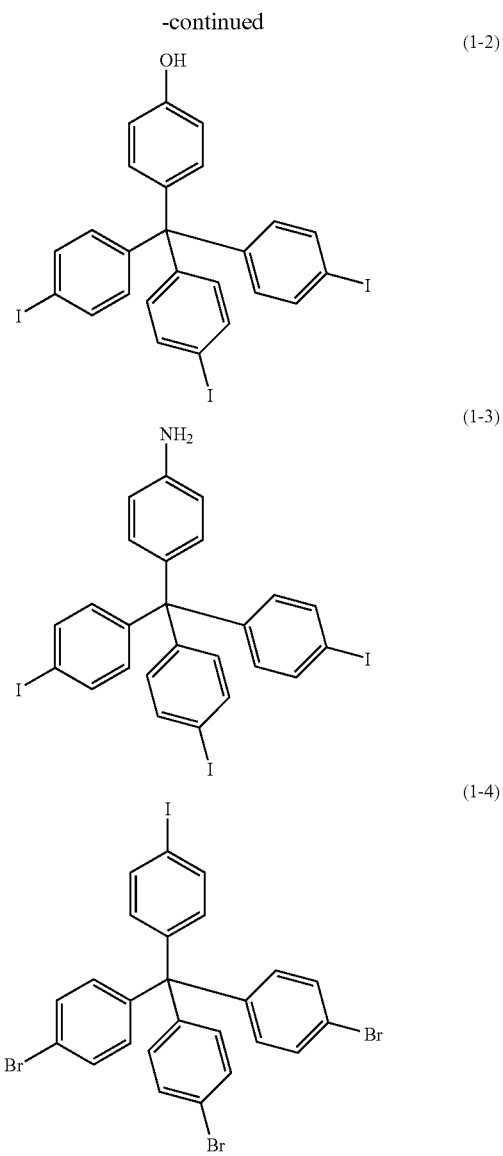

By using the compound of the present invention as a starting material, in particular when X and/or Y are halogen atoms, it is possible to incorporate, by a Sonogashira reaction, an acetylene compound that can impart high heat resistance or, by a Suzuki coupling reaction, an aromatic compound.

Furthermore, by using the compound of the present invention as a starting material, when X and/or Y are a hydroxy group or an amino group it is possible to readily form an aromatic ester compound, an aromatic amide compound, or an aromatic imide compound.

A process for producing a compound represented by Formula (1) above is not particularly limited and, for example, the processes below can be cited as preferred examples.

As one example of the process for producing a compound represented by Formula (1) above, there can be cited a production process comprising a step of obtaining tris(4-aminophenyl)methanol and/or a salt thereof by adding water to pararosaniline hydrochloride under acidic conditions, a step of obtaining a tridiazonium salt by diazotizing the tris(4-aminophenyl)methanol and/or salt thereof, a step of obtaining a substituted derivative by replacing a diazonium group of the tridiazonium salt with a hydroxy group or a halogen atom, and a step of reacting the substituted derivative and a monosubstituted benzene under acidic conditions.

Pararosaniline hydrochloride is a commercial compound, and since it is an inexpensive compound, it is excellent in terms of cost.

The acid used in the above reaction of pararosaniline hydrochloride is not particularly limited as long as the reaction progresses, but in terms of the price of the reagent and the cost arising from reaction equipment, etc. it is preferably an inorganic acid, and sulfuric acid is more preferable.

The tris(4-aminophenyl)methanol and/or salt thereof may be or may not be isolated.

It is preferable to use a nitrite for diazotization of the tris(4-aminophenyl)methanol and/or salt thereof, and in particular in terms of safety and cost it is more preferable to use sodium nitrite. Furthermore, the diazotization is preferably carried out under acidic conditions.

The counteranion of the diazonium of the tridiazonium salt obtained by the diazotization is not particularly limited, and may form any salt in the reaction system. Moreover, the tridiazonium salt may be or may not be isolated, but it is preferable that it is not isolated since there are cases in which, depending on the type of counteranion, the diazonium group is very unstable toward humidity, etc.

As the substitution reaction of the diazonium group, an iodination reaction in which as a reagent an iodide salt (preferably potassium iodide) is used, a bromination reaction in which copper (I) bromide is used, a chlorination reaction in which copper (I) chloride is used, a fluorination reaction in which, after a tetrafluoroboric acid salt is formed using tetrafluoroboric acid, the tetrafluoroboric acid salt is thermally decomposed, a hydroxylation reaction in which water and a copper compound are used, etc. can be cited. Among them, an iodination reaction in which an iodide salt is used or a bromination reaction in which copper (I) bromide is used is preferable.

Examples of the monosubstituted benzene used in the step of reacting the substituted derivative and a monosubstituted benzene under acidic conditions include phenol, aniline, fluorobenzene, chlorobenzene, bromobenzene, and iodobenzene. Among them, from the viewpoint of reactivity, phenol or aniline is preferable. Furthermore, from the viewpoint of controlling reaction rate and side reactions the monosubstituted benzene is preferably used in an amount of solvent.

Moreover, the acid used in the step of reacting the substituted derivative and a monosubstituted benzene under acidic conditions is not particularly limited as long as the reaction progresses, but in terms of the price of the reagent and the cost arising from reaction equipment, etc. a metallic Lewis acid or an inorganic acid is preferable, and sulfuric acid is more preferable.

As another example of the process for producing a compound represented by Formula (1) above, there can be cited a production process comprising a step of obtaining a diazonium salt by diazotizing 4-tritylaniline, a step of obtaining a substituted derivative by replacing a diazonium group of the diazonium salt with a halogen atom, and a step of reacting the substituted derivative with bromine or iodine.

4-Tritylaniline is a commercial compound, and since it is an inexpensive compound, it is excellent in terms of cost.

The diazotization of 4-tritylaniline and the substitution reaction of the diazonium group are the same as described above except that the starting materials are different, and preferred ranges are also the same.

In the step of reacting the substituted derivative with bromine or iodine, due to the reactivity and steric hindrance of a benzene ring, bromine or iodine reacts with the 4-position of an unsubstituted benzene ring of the substituted derivative, and a compound in which a bromine atom or an iodine atom is introduced into the 4-position of each of the three unsubstituted benzene rings may be obtained.

In each step of the above-mentioned two examples of the production process, a known solvent may be used as necessary. Moreover, termination of the reaction may be carried out by a known quenching method.

Furthermore, the above-mentioned two examples of the production process may comprise steps of isolation, neutralization, drying, and/or purification as necessary.

In accordance with the present invention, there can be provided a novel tetraphenylmethane skeleton-containing compound.

EXAMPLES

The present invention is explained more specifically below by reference to Examples, but the present invention should not be construed as being limited to these Examples.

Example 1

Synthesis of 4-bromophenyl[tris(4-iodophenyl)]methane

4-Bromophenyl[tris(4-iodophenyl)]methane was synthesized in accordance with the scheme below.

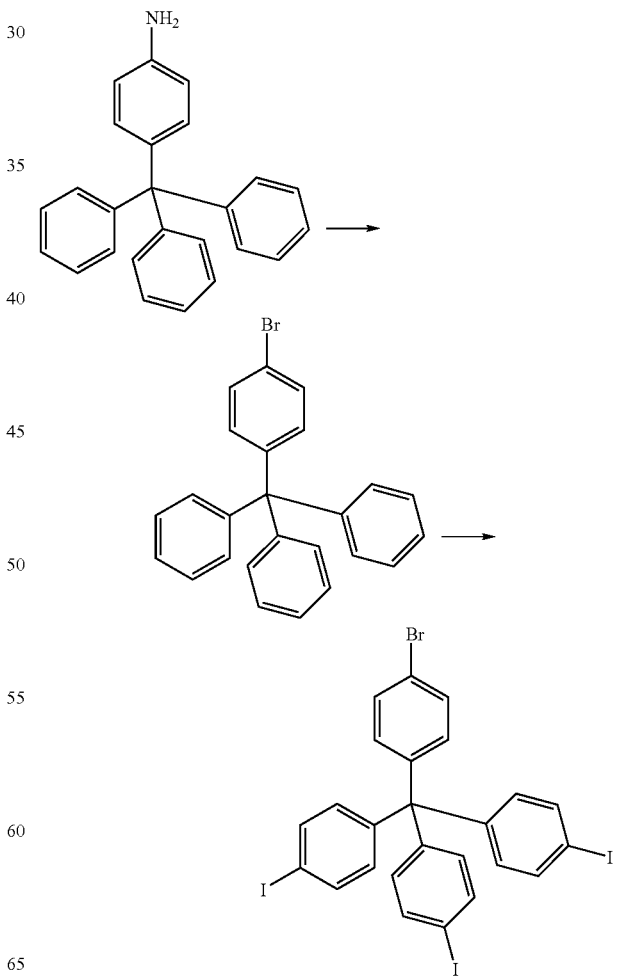

Synthesis of 4-tritylbromobenzene 25 parts by weight of 4-tritylaniline, 400 parts by weight of acetone, and 162 parts by weight of hydrobromic acid were put into a reaction vessel and stirred. While cooling the vessel in an ice bath, a solution of 7 parts by weight of sodium nitrite dissolved in 100 parts by weight of water was slowly added dropwise thereto. After the dropwise addition was complete, stirring was carried out for 30 minutes in an ice bath. Slowly added dropwise to this solution in an ice bath was a solution of 17.4 parts by weight of copper (I) bromide that had been dissolved in 31.5 parts by weight of hydrobromic acid. After the dropwise addition was complete, stirring was carried out at room temperature for 2 hours. After the reaction, a precipitate deposited in the reaction solution was collected by filtration, thus giving 25.8 parts by weight of 4-tritylbromobenzene (yield: 86%).

$^1$H-NMR (CDCl$_3$) δ=7.00 (d, 2H), 7.10-7.30 (m, 15H), 7.38 (d, 2H).

Synthesis of 4-bromophenyl[tris(4-iodophenyl)]methane 40 parts by weight of 4-tritylbromobenzene, 90.3 parts by weight of bis(triacetoxy)iodobenzene, 58.4 parts by weight of iodine, and 800 parts by weight of chloroform were put in a reaction vessel and refluxed for 6 hours. A further 90.3 parts by weight of bis(triacetoxy)iodobenzene was added to the reaction solution and refluxing was carried out for 12 hours. After the reaction, a precipitate deposited in the reaction liquid was collected by filtration, thus giving 65 parts by weight of 4-bromophenyl[tris(4-iodophenyl)]methane (yield: 85%).

$^1$H-NMR (CDCl$_3$) δ=6.88 (d, 6H), 7.01 (d, 2H), 7.38 (d, 6H), 7.58 (d, 2H).

Example 2

Synthesis of 4-hydroxyphenyl[tris(4-iodophenyl)]methane

4-Hydroxyphenyl[tris(4-iodophenyl)]methane was synthesized in accordance with the scheme below.

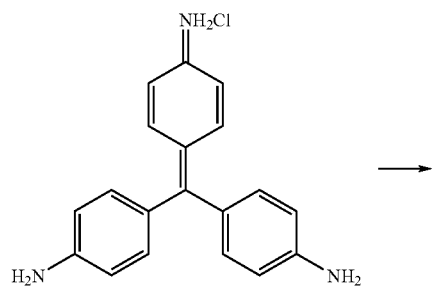

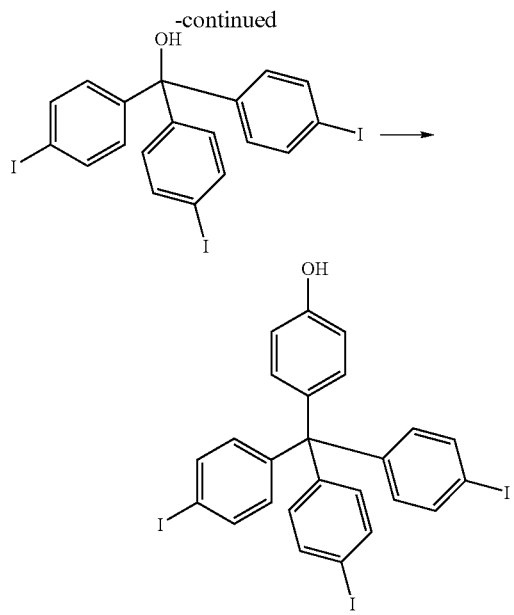

Synthesis of tris(4-iodophenyl)methanol 10 parts by weight of pararosaniline hydrochloride, 35.4 parts by weight of conc. sulfuric acid, and 56 parts by weight of water were put into a reaction vessel and stirred. While cooling the vessel in an ice bath, a solution of 7 parts by weight of sodium nitrite dissolved in 23 parts by weight of water was slowly added dropwise thereto. After the dropwise addition was complete, stirring was carried out in an ice bath for 30 minutes. Slowly added dropwise to this solution in an ice bath was a solution of 56 parts by weight of potassium iodide that had been dissolved in 31.5 parts by weight of water. After the dropwise addition was complete, stirring was carried out at room temperature for 5 hours, and stirring was carried out for a further 30 minutes while heating at 80° C. After the reaction, a precipitate deposited in the reaction liquid was collected by filtration and purified by column chromatography (normal hexane ethyl acetate=9:1), thus giving 5.9 parts by weight of tris(4-iodophenyl)methanol (yield: 30%).

$^1$H-NMR (CDCl$_3$) δ=6.99 (d, 6H), 7.65 (d, 6H).

Synthesis of 4-hydroxyphenyl[tris(4-iodophenyl)]methane 10 parts by weight of tris(4-iodophenyl)methanol, 4.4 parts by weight of phenol, and 2 parts by weight of conc. sulfuric acid were put into a reaction vessel and stirred for 4 hours while heating at 80° C. After cooling, a 10% sodium hydroxide solution was added to the reaction solution, and stirring was carried out for 2 hours. A deposited precipitate was collected by filtration, thus giving 8.5 parts by weight of 4-hydroxyphenyl[tris(4-iodophenyl)]methane (yield: 76%).

$^1$H-NMR (CDCl$_3$) δ=6.71 (d, 2H), 6.88 (d, 6H), 6.96 (d, 2H), 7.57 (d, 6H).

Example 3

Synthesis of 4-aminophenyl[tris(4-iodophenyl)]methane 4-aminophenyl[tris(4-iodophenyl)]methane was synthesized in accordance with the scheme below.

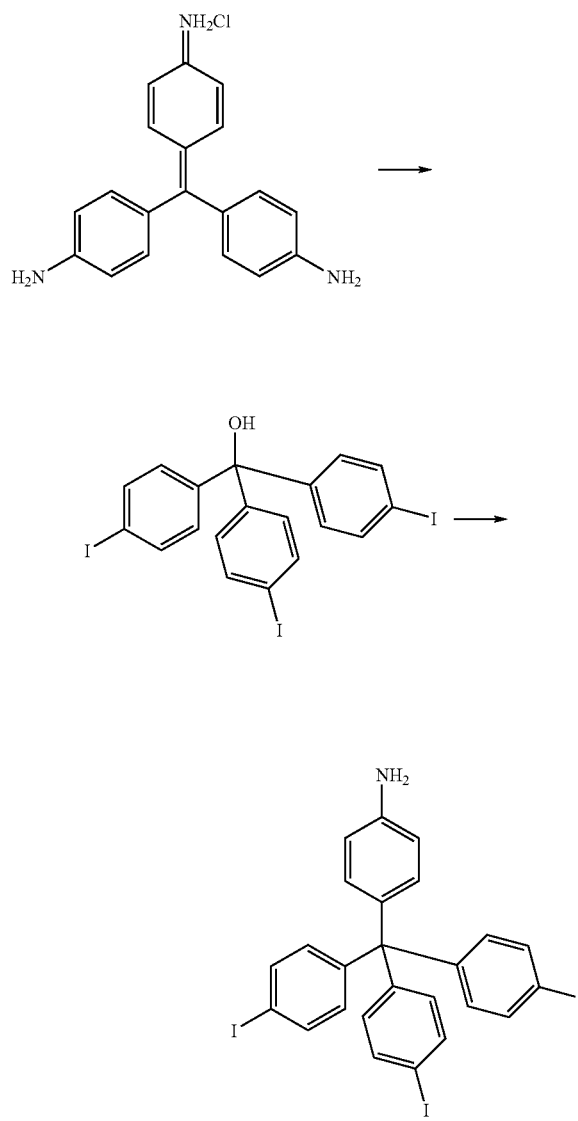

89 parts by weight of tris(4-iodophenyl)methanol and 500 parts by weight of aniline were put into a reaction vessel and stirred for 4 hours while heating at 190° C. 350 parts by weight of ethanol was added thereto, and stirring was carried out for 1 hour while heating at 90° C. After cooling, a deposited solid was collected by filtration and washed with methanol, thus giving 100 parts by weight of 4-aminophenyl[tris(4-iodophenyl)]methane (yield: 93%).

$^1$H-NMR (CDCl$_3$) δ=6.55 (d, 2H), 6.88 (d, 6H), 6.96 (d, 2H), 7.65 (d, 6H).

Example 4

Synthesis of tris(4-bromophenyl)](4-iodophenyl)methane

[Tris(4-bromophenyl)](4-iodophenyl)methane was synthesized in accordance with the scheme below.

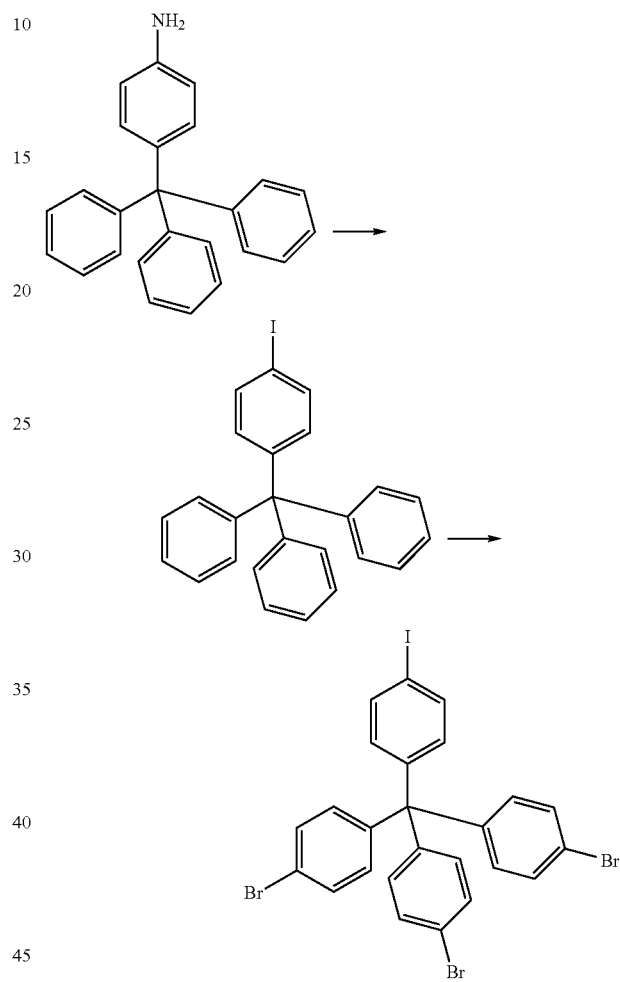

Synthesis of 1-iodo-4-tritylbenzene

1-Iodo-4-tritylbenzene was synthesized by reference to Q. Li, A. V. Rukavishnikov, P. A. Petukhov, T. O. Zaikova, and J. F. W. Keana, Org. Lett., 4, 3631 (2002).

Synthesis of [tris(4-bromophenyl)](4-iodophenyl)methane 55 parts by weight of 1-iodo-4-tritylbenzene and 100 parts by weight of bromine were added to a reaction vessel and stirred at room temperature for 30 minutes. The reaction solution was added to 100 parts by weight of ethanol at −20° C., and stirring was carried out at that temperature for 2 hours. A deposited solid was collected by filtration and washed with 1 mol/L sodium thiosulfate aqueous solution and water, thus giving 84 parts by weight of [tris(4-bromophenyl)](4-iodophenyl)methane.

$^1$H-NMR (CDCl$_3$) δ=6.88 (d, 2H), 7.01 (d, 6H), 7.39 (d, 6H), 7.59 (d, 2H).

What is claimed is:
1. A compound represented by Formula (1-2) below:
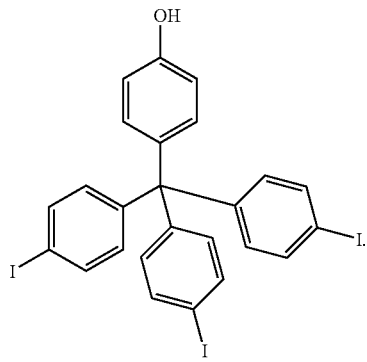
2. A compound represented by Formula (1-3) below:
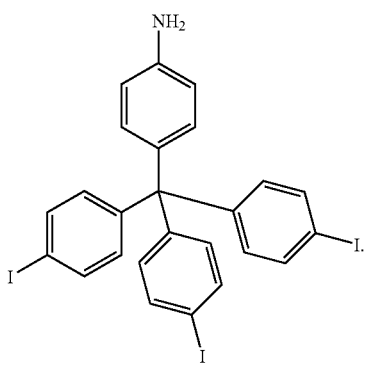
* * * * *